(12) United States Patent
Feith et al.

(10) Patent No.: US 11,957,863 B2
(45) Date of Patent: *Apr. 16, 2024

(54) LUER HAVING MICROBORE TUBING RETENTION POCKET BOND WITH AXIAL SPLINE

(71) Applicant: CareFusion 303, Inc., San Diego, CA (US)

(72) Inventors: Raymond P. Feith, Chino Hills, CA (US); Randall D. Kipp, Upland, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/513,578

(22) Filed: Oct. 28, 2021

(65) Prior Publication Data

US 2022/0054816 A1    Feb. 24, 2022

Related U.S. Application Data (63) Continuation of application No. 16/378,351, filed on Apr. 8, 2019, now Pat. No. 11,185,675.

(51) Int. Cl.
*A61M 39/10* (2006.01)
*A61M 25/00* (2006.01)
(Continued)

(52) U.S. Cl.
CPC ........ *A61M 39/1011* (2013.01); *A61M 39/10* (2013.01); *A61M 39/12* (2013.01);
(Continued)

(58) Field of Classification Search
CPC .............. A61M 39/10; A61M 25/0097; A61M 2025/0042; A61M 39/12; A61M 39/1011;
(Continued)

(56) References Cited

U.S. PATENT DOCUMENTS

| 4,452,473 A | * | 6/1984 | Ruschke ............... A61M 39/10 |
| | | | 604/905 |
| 5,176,415 A | | 1/1993 | Choksi |

(Continued)

FOREIGN PATENT DOCUMENTS

| CN | 109475730 A | 3/2019 |
| EP | 0471574 | 2/1992 |

(Continued)

OTHER PUBLICATIONS

International Search Report and Written Opinion for Application No. PCT/US2020/025279, dated Jun. 30, 2020, 13 pages.

(Continued)

*Primary Examiner* — William R Carpenter
*Assistant Examiner* — Robert F Allen
(74) *Attorney, Agent, or Firm* — Morgan, Lewis & Bockius LLP (57) ABSTRACT

A connector is disclosed that includes comprising a body having a tubing portion, a luer portion axially opposite the tubing portion and connected thereto, and an inner circumferential surface defining an internal bore of the connector. The inner circumferential surface extends axially between the tubing portion and the luer portion, and the internal bore being is in fluid communication with the tubing portion and the luer portion. The inner circumferential surface includes a plurality of splines extending axially along a length of the inner circumferential surface in the tubing portion of the connector. The inner circumferential surface is configured to engage an external surface of a tubing in a coupled configuration. In the coupled configuration edges of the splines grip and engage the external surface of the tubing to retain the tubing in the body.

14 Claims, 5 Drawing Sheets

(51) Int. Cl.
*A61M 39/12* (2006.01)
*B29C 45/26* (2006.01)
*B29C 59/02* (2006.01)

(52) U.S. Cl.
CPC . *A61M 2025/0042* (2013.01); *A61M 25/0097* (2013.01); *B29C 45/2628* (2013.01); *B29C 59/021* (2013.01)

(58) Field of Classification Search
CPC . B29C 45/2628; B29C 65/4895; B29C 65/48; B29C 59/021; F16D 2001/103; C08J 5/122
See application file for complete search history.

(56) References Cited

U.S. PATENT DOCUMENTS

| | | | |
|---|---|---|---|
| 5,344,412 A | | 9/1994 | Wendell |
| 5,620,427 A | | 4/1997 | Werschmidt et al. |
| 6,152,913 A | | 11/2000 | Feith et al. |
| 8,038,182 B2 * | | 10/2011 | Kurimoto ............. A61M 39/10 |
| | | | 285/332 |
| 9,163,759 B2 * | | 10/2015 | Thomas ................ F16L 19/065 |
| 10,086,154 B2 | | 10/2018 | Mantell |
| 11,185,675 B2 * | | 11/2021 | Feith .................... A61M 39/12 |
| 2002/0032436 A1 | | 3/2002 | Mogg |
| 2006/0271015 A1 | | 11/2006 | Mantell |
| 2011/0121558 A1 * | | 5/2011 | Kanner ................... F16L 37/02 |
| | | | 285/24 |
| 2012/0209252 A1 * | | 8/2012 | Nikitina ................ A61M 39/10 |
| | | | 137/15.01 |
| 2015/0335873 A1 * | | 11/2015 | Khalaj .................. A61M 39/12 |
| | | | 604/533 |
| 2018/0086905 A1 | | 3/2018 | Zhang |
| 2019/0083721 A1 | | 3/2019 | Mantell |

FOREIGN PATENT DOCUMENTS

| | | |
|---|---|---|
| JP | 2012213867 A | 11/2012 |
| JP | 2017515564 A | 6/2017 |
| JP | 2018175544 A | 11/2018 |
| WO | WO-2015179180 | 11/2015 |

OTHER PUBLICATIONS

Canadian Office Action for Application No. 3136257, dated Jul. 11, 2023, 5 pages.
Japanese Office Action for Application No. 2021-559394, dated Oct. 20, 2023, 7 pages including translation.

* cited by examiner

LUER HAVING MICROBORE TUBING RETENTION POCKET BOND WITH AXIAL SPLINE

CROSS REFERENCE TO RELATED APPLICATIONS

The present application is a continuation patent application of U.S. patent application Ser. No. 16/378,351 entitled "LUER HAVING MICROBORE TUBING RETENTION POCKET BOND WITH AXIAL SPLINE," filed on Apr. 8, 2019, issued as U.S. Pat. No. 11,185,675 on Nov. 30, 2021, which is incorporated herein by reference in its entirety.

TECHNICAL FIELD

The present disclosure generally relates to medical connectors, and more particularly, to a medical connector having a retaining mechanism for preventing a tubing coupled thereto from dislodging or separating from the connector due to the reduction of fluid in the tubing and a sealing mechanism to prevent fluid from inadvertently leaking between the tubing and connector.

BACKGROUND

In the medical field, fluids are frequently administered as infusions. The container holding the medical fluid, such as a flexible intravenous (IV) bag, is connected to an infusion device, such as an IV needle, by a disposable IV set comprising tubing having one or more fittings or connectors. IV sets may also have intermediate ports or connection points where additional fluid containers may be connected to introduce or withdraw fluid. The tubing is connected to the fittings or connectors by one or more forms of mechanical attachment, that is inserted into the interior of the tubing, and bonding, such as a solvent weld between an internal pocket of the fitting and the exterior surface of the tubing.

Medical connectors are widely used in fluid delivery systems such as those used in connection with intravenous (IV) fluid lines, blood access, hemodialysis, peritoneal dialysis, enteral feeding, drug vial access, etc. Medical connectors may generally connect two fluid lines or tubing.

SUMMARY

The medical connector may be a hollow tubular structure that receives a fluid line or tubing at one end thereof. The connector provides a flow path for fluid entering from the tubing to exit the connector from the opposite end thereof. The presence of fluid in the tubing may create a hermetic seal between outer surface of the tubing and the inner surface of the medical connector. The seal may prevent the tubing from separating from the medical connector. However, when the fluid is absent in the tubing or when the amount of fluid in the tubing is reduced, the seal may be weakened and the tubing may be separated easily from the connector, thereby creating a "free flow" leak.

Furthermore, where microbore tubing is used, the minimal surface area of the microbore tubing for bonding presents additional challenges to retaining the microbore tubing in the connector.

One or more embodiments include a connector including a body having a tubing port and a luer port, an internal bore extending axially between the tubing port and the luer port, a plurality of axial splines extending linearly along a first portion of the internal bore, and a plurality of axial channels disposed between the plurality of axial splines, wherein a depth of each axial channel tapers in a direction towards the tubing port, and wherein edges of the plurality of axial splines are configured to engage and grip an external surface of a tubing to retain the tubing in the body.

One or more embodiments include a connector having a body including a tubing profile, a luer profile, a restriction interposed between the luer profile and the tubing profile, the restriction including a projection, and an internal longitudinal bore in at least the tubing profile, the internal longitudinal bore comprising a plurality of splines extending linearly along a length of the tubing profile such that the plurality of splines extends parallel with the internal longitudinal bore, wherein the projection extends into the internal bore and the projection is configured to engage and grip a tubing to create a seal between the restriction and the tubing.

One or more embodiments include a method of manufacturing a connector, including providing a first core pin and a second core pin, the first core pin having a first core pin body having a luer-shaping portion and a restriction-shaping portion connected to each other, and the second core pin having a second core pin body having a base portion and a tubing-shaping portion connected to each other, wherein a plurality of axially extending teeth and axially extending recesses are formed along a radial exterior of the tubing-shaping portion, inserting the first core pin into a first portion of a malleable material forming the luer portion of the connector, and inserting the second core pin into a second portion of the malleable material forming the tubing portion of the connector, the first and the second core pins being axially aligned and inserted into the malleable material from opposite ends, and contacting the axially extending teeth and axially extending recesses with the malleable material forming the tubing portion of the connector to define a plurality of axial splines and a plurality of recesses in an internal bore of the connector.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Various embodiments of the present disclosure are directed to providing a connector having greater tubing retention for IV sets that use microbore tubing which has minimal surface area for bonding.

Various embodiments of the present disclosure are additionally directed to providing connector having improved sealing capabilities so as to prevent fluid from inadvertently leaking between the external surface of the tubing (e.g., microbore tubing) and the internal surface of the connector.

Embodiments disclosed are directed to a connector having a retaining mechanism for preventing a microbore tubing coupled thereto from dislodging and/or separating from the connector in the absence (or reduction) of fluid in the tubing. Embodiments disclosed herein are further directed to a connector having a restriction mechanism to retain the tubing in the connector and seal between the tubing and the inner surface of the connector. As disclosed herein, the retaining mechanism may include a plurality of splines extending axially along an inner circumference of a tubing portion of the connector. As the fluid line (tubing) is inserted into the tubing portion, edges of the axial splines may dig into and grip the tubing for greater tubing retention within the tubing portion of the connector. For example, the fluid line may be inserted into the tubing portion with an interference fit whereby the outer diameter of the fluid line is slightly larger than the inner diameter of the tubing portion. As a result, a relatively stronger tensile force is required to be exerted on the tubing to separate or dislodge the tubing from the connector. Thus, accidental separation of the tubing may be minimized.

Further advantageously, adjacent neighboring splines define a corresponding recesses or channels therebetween similarly extending axially along an inner circumference of the tubing portion of the connector. As such, an increased amount of solvent for bonding the fluid line or tubing to the tubing portion may be collected into the channels for maximum boding. This will insure a uniform spread of solvent and eliminate possible squeegee of fluid on the bonding surface. This is in contrast to conventional connector and fluid line bonding techniques where the solvent is flowed into the connector and once the tubing is inserted into the connector, the solvent is subject to squeegee by the tubing, thereby reducing surface area of the solvent between the tubing and the connector for bonding.

As disclosed herein, the restraining mechanism may include radial projections, sealing rings, or alternatively barbed fittings, barbed edges, or similar structures that may retain the tubing. The restriction mechanism ensures that a seal is maintained between the tubing and the inner surface of the connector during low pressure conditions (e.g., during the absence of fluid in the tubing) since there is an interference fit between the tubing and the connector. As a result, a relatively stronger tensile force is required to be exerted on the tubing to separate or dislodge the tubing from the connector. Thus, accidental separation of the tubing is minimized.

In some embodiments, the restriction mechanism may include one or more radial projections or ledges on an internal surface of the connector that limits the extent of the tubing in the connector when inserted therein. As discussed below, the connector at the end opposite to the end receiving the tubing may include a female luer fitting. The restriction mechanism prevents the tubing from extending into the female luer fitting during assembly and thereby ensures correct operation of the medical connector.

Another advantage of the medical connector, according to embodiments disclosed, is that there is not a substantial increase in the manufacturing costs of the medical connector. Existing manufacturing equipment may be modified at minimal costs to manufacture the example medical connector. For example, the core pins of the injection molding equipment used to manufacture the medical connector may be redesigned to create the axial splines and channels, and the restraining mechanisms.

As used herein, the terms "tubing," "fluid line," and any variation thereof refers to medical lines or tubes used to deliver liquids, solvents, or fluids (including gas) to or from a patient under medical care. For example, fluid lines (tubing) may be used for intravenous (IV) delivery of fluids, fluid drainage, oxygen delivery, a combination thereof, and the like.

As used herein, the terms "medical connector," "connector," "fitting," and any variation thereof refer to any device used to provide a fluid flow path between two or more fluid lines coupled thereto. For example, the medical connector may be or include a bond pocket or other types of connectors.

Figure 1:
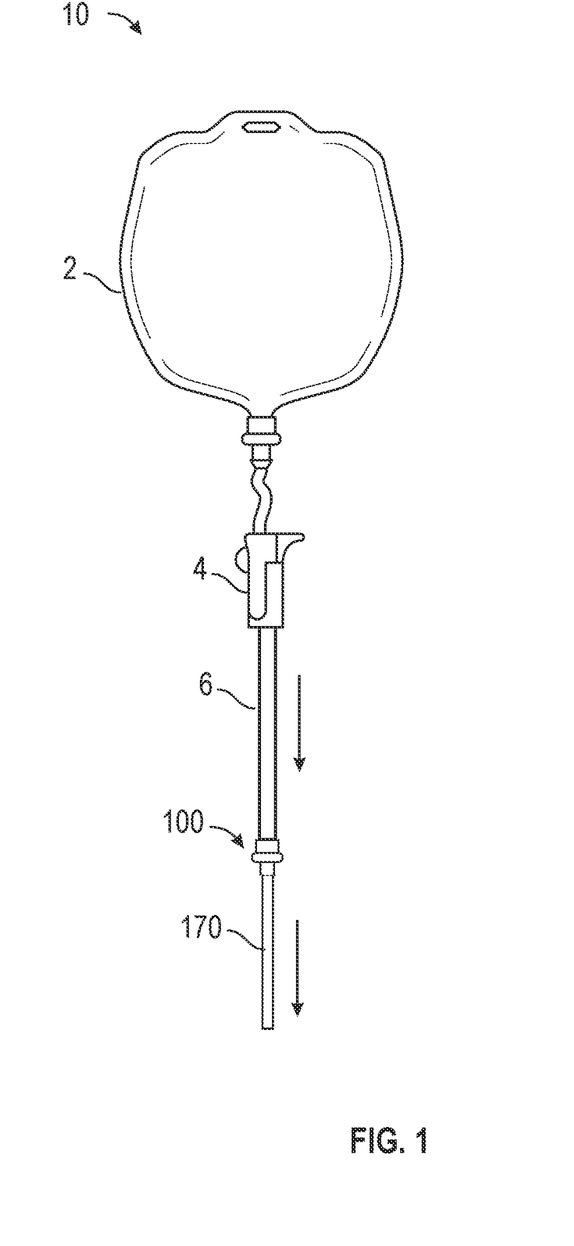
FIG. 1 depicts a perspective view of an IV set having a medical connector that may employ the principles of the present disclosure, in accordance with some embodiments of the present disclosure.

FIG. 1 depicts a perspective view of an IV set 10 having a medical connector 100 that may employ the principles of the present disclosure, in accordance with some embodiments of the present disclosure. As depicted, the IV set may include a fluid source such as a fluid bag 2 which may include or contain saline solution or other fluid to be administered to a patient. As illustrated, a first tubing 6 carries flow from a drip chamber 4, through connector 100, and into a second fluid line or tubing 170. An IV pump (not shown) receives fluid from fluid bag 2 via second tubing 170, and controls and dispenses the fluids therefrom to a patient. As shall be described in further detail below, a tubular portion of the connector 100 has an internal bore configured to receive the second tubing 170. For the purposes of the present disclosure, the second tubing 170 will be described as microbore or smallbore tubing, and the connector 100 will thus be described as being configured to receive and retain microbore tubing. However, the various embodiments of the connector described herein may be applied to other types of tubing, e.g. macrobore or largebore tubing.

Figure 2:
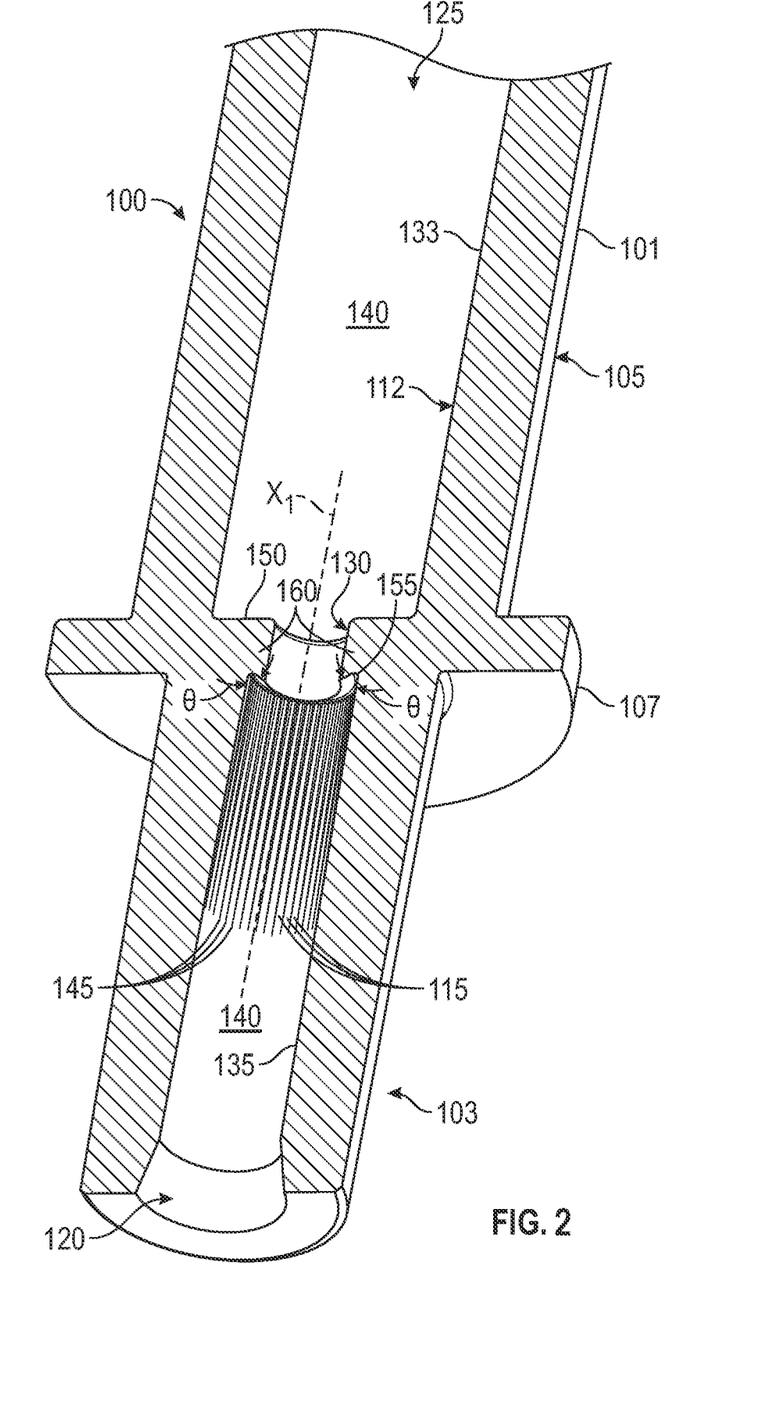
FIG. 2 is a cross-sectional view of the medical connector of FIG. 1, in accordance with some embodiments of the present disclosure.

FIG. 2 illustrates a cross-sectional view of the medical connector 100 of FIG. 1, according to embodiments disclosed. As illustrated, the medical connector 100 (or simply, connector) may include a generally cylindrical body 101 having a "first" or tubing portion 103 and a "second" or luer portion 105 axially opposite the tubing portion 103 and connected thereto. In some embodiments, the body 101 may also include a grip 107 disposed along the outer surface of the body 101. The tubing portion 103 may include a tubing port 120 that is sized and shaped or otherwise configured to receive a fluid line (referred to hereafter as "tubing"), as discussed below. Similarly, the luer portion 105 may include a luer port 125 that is sized and shaped or otherwise configured to receive a male luer connector. As depicted, the body 101 defines an internal longitudinal passageway or bore 140 extending from the tubing port 120 to the luer port 125 and fluidly connecting the tubing port 120 and the luer port 125 with each other.

In the depicted embodiments, the internal bore 140 is defined by the inner circumferential surface 112 of the body 101 and is continuous from the tubing port 120 to the luer port 125. In some embodiments, the inner circumferential surface 112 in the tubing portion 103 and the luer portion 105 has two non-similar profiles. Specifically, the inner circumferential surface 112 in the tubing portion 103 has a tubing profile 135 and the inner circumferential surface 112 in the luer portion 105 has a luer profile 133. The tubing profile 135, and thereby the tubing portion 103 of the connector 100, is sized and shaped (or otherwise configured) to receive a tubing. In particular, the tubing profile 135 may be sized, shaped, and otherwise configured to receive a microbore tubing 170 (described in further detail below). For example, tubing having an inner diameter of less than 0.100 inches, and particularly tubing having an outer diameter of approximately 0.079 inches or less, is considered "smallbore" or "microbore" and is bonded into a tubing pocket such as the internal bore 140 defined in tubing profile 135. Tubing having an inner diameter of greater than 0.100 inches is typically considered "macrobore." Exemplary embodiments of the present disclosure are illustrated and described herein with respect to a tubing that is in the form of a "smallbore" or "microbore" tubing and a pocket bond for a "smallbore" or "microbore" tubing. However, the various embodiments of the present disclosure are not limited to the aforementioned configuration and may similarly be applied to "largebore" or "macrobore" tubing and related connectors, as well as any other intermediate size tubings and connectors between "microbore" and "macrobore" connectors. The luer profile 133, and thereby the luer portion 105 of the connector 100, may be sized and shaped (or otherwise configured) to receive male luer fittings. The luer profile 133, and thereby the luer portion 105, may be ISO-594 compliant.

During assembly, in order to limit the extent of the tubing inserted, advanced, or otherwise "slipped" into the connector 100, the inner circumferential surface 112 may include a restriction mechanism (hereafter referred to as "restriction 130"). The restriction 130 may be defined to protrude radially inward from the inner circumferential surface 112, and may be interposed between the luer profile 133 and the tubing profile 135. In some embodiments, the restriction 130 serves as a stop for the insertion of tubing into the internal bore 140 defined in the luer profile 133. Accordingly, restriction 130 may have a diameter D2 (illustrated in FIG. 6) that is smaller than the smallest diameter D1 of the internal bore 140 defined in the tubing profile 135.

In accordance with some embodiments, the tubing profile 135 of the tubing portion 103 may include a retaining mechanism for improving the ability of the connector 100 to retain the microbore tubing 170 inserted therein and thereby prevent the microbore tubing 170 from separating (or otherwise dislodging) from the connector 100. For example, the retaining mechanism may prevent the microbore tubing 170 from separating (or otherwise dislodging) from the connector 100 during a low pressure condition in the tubing created due to a reduction in the fluid in the tubing. In an example, and as illustrated, the retaining mechanism may be or include a plurality of splines 115 axially extending axially along the inner circumferential surface 112 of the tubing portion 103 of connector 100. As the microbore tubing 170 (illustrated in FIG. 5) is inserted into the tubing portion 103 of the connector 100, inner circumferential surface 112 in the tubing portion 103 is configured to engage an external surface of the microbore tubing 170 in a coupled configuration. For example, as the microbore tubing 170 is inserted into the tubing portion 103, edges 137 of the axial splines 115 may dig into and grip the exterior surface of the tubing for greater tubing retention within the tubing portion of the connector. Thus, in the coupled configuration, the microbore tubing 170 may be inserted into the tubing portion with an interference fit such that edges 137 of the axial splines 115 dig into, grip and engage the external surface of the microbore tubing 170 to retain the microbore tubing 170 in the tubing portion 103 of the connector 100. The aforementioned configuration provides the advantage that once the edges 137 of the axial splines 115 dig into, grip and engage the external surface of the microbore tubing 170, friction between the microbore tubing 170 and inner circumferential surface 112 is increased such that the microbore tubing 170 may not be easily dislodged from the connector 100, without departing from the scope of the disclosure. For example, by biting or digging into the external surface of the microbore tubing 170, the axial splines may increase the friction between the connector 100 and the microbore tubing 170 when a tensile force (direction indicated by the arrow F, illustrated in FIG. 5) is applied on the microbore tubing 170 to remove it from the connector 100. Advantageously as a result, the tensile force required to remove or otherwise dislodge the microbore tubing 170 from the connector 100 is increased and thus the microbore tubing 170 is better secured and retained in the connector 100. Further, fluid in the microbore tubing 170 may exert pressure in a radially outward direction, which may further increase the friction between the microbore tubing 170 and the inner circumferential surface 112.

In accordance with some embodiments, adjacent neighboring splines 115 define corresponding recesses or channels 145 therebetween. The channels 145 similarly extend axially along the inner circumferential surface 112 of the tubing portion 103 of connector 100. Advantageously, an increased amount of solvent for bonding the microbore tubing 170 to the inner circumferential surface 112 defined in the tubing portion 103 may be collected into the channels 145 for maximum bonding. In particular, collecting the solvent in the channels 145 allows for an increased amount of solvent available for bonding of the microbore tubing 170 to the inner circumferential surface 112 of the tubing portion 103. Providing the channels 145 with the solvent collected therein will yield a uniform spread of solvent and eliminate possible squeegee of fluid on the bonding surface of the tubing portion 103. Thus, a maximum amount of solvent remains available for bonding the microbore tubing 170 to the inner circumferential surface 112 of the tubing portion 103, and an even greater tubing retention may be achieved. This is in contrast to conventional connector and tubing bonding techniques where the solvent is flowed into the connector and once the fluid line/tubing is inserted into the connector, the solvent is subject to squeegee by the tubing, thereby reducing surface area of the solvent between the tubing and the connector.

Figure 3:
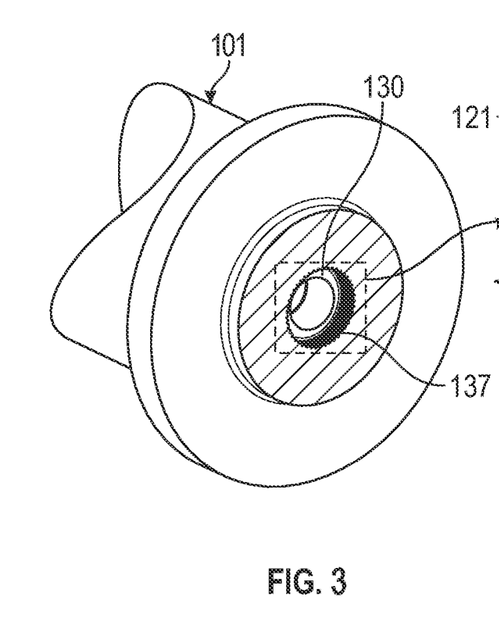
FIG. 3 is a partial cross-sectional view of axial splines and channels of the tubing section of the connector of FIG. 2, in accordance with some embodiments of the present disclosure.
Figure 4:
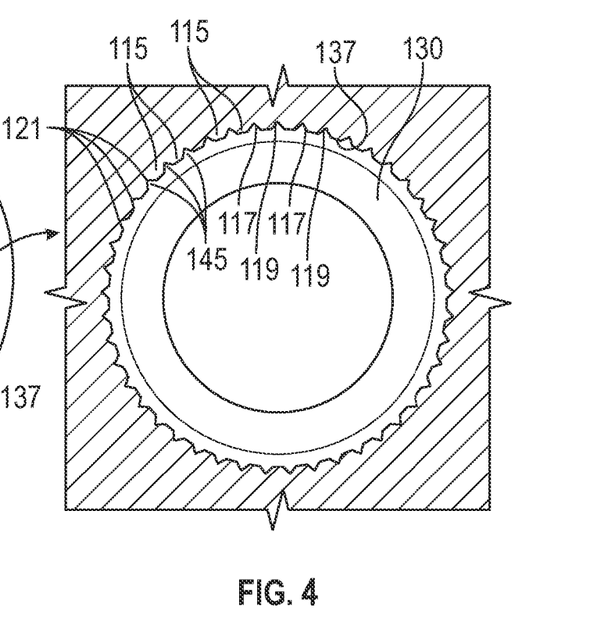
FIG. 4 is an enlarged partial view of the axial splines and channels of the tubing section of the connector of FIG. 2, in accordance with some embodiments of the present disclosure.

FIG. 3 is a partial cross-sectional view of axial splines and channels of the tubing section of the connector of FIG. 2, in accordance with some embodiments of the present disclosure. FIG. 4 is an enlarged partial view of the axial splines and channels of the tubing section of the connector of FIG. 2, in accordance with some embodiments of the present disclosure.

Referring to FIGS. 3 and 4, with continued reference to FIG. 2, each of the axial splines may be defined by a first inclined surface 117, a second inclined surface 119 and the edge 137 interposed between the first and second inclined surface 117 and 119. As depicted, the axial splines may be formed in the shape of teeth of a spline gear. Since the channels 145 are defined between adjacent splines 115, each of the channels 145 are defined by adjacent first and second inclined surfaces 117 and 119 meeting at a vertex 121. However, the shapes of the axial splines 115 and channels 145 is not limited to the aforementioned configuration. For example, the axial splines 115 and channels 145 may not be restricted to any particular shape or size as long as the axial splines 115 have a shape so as to "bite into," "dig into," grip, or otherwise engage the outer surface of the microbore tubing 170, and as long as the channels 145 form a recess of sufficient depth to contain a solvent therewithin.

In accordance with some embodiments, the axial splines 115 and channels 145 may be disposed at regular intervals along the inner circumferential surface 112 of the tubing portion 103. However, in other embodiments, the axial splines 115 and channels 145 may be disposed at irregular intervals along the inner circumferential surface 112 of the tubing profile 135.

In accordance with some embodiments, an angle α between the first inclined surface 117 and the second inclined surface 119 of adjacent splines ranges from about 30 degrees to 150 degrees, more typically about 60 degrees to 120 degrees, 80 degrees to 100 degrees, or in some cases approximately 90 degrees. Though recited in terms of certain ranges, it will be understood that all ranges from the lowest of the lower limits to the highest of the upper limits are included, including all intermediate ranges or specific angles, within this full range or any specifically recited range.

In some embodiments, a height of each of the splines as measured from the vertex 121 to the edge 137 of each spline may range from about 0.0001 inches to 0.002 inches, more typically about 0.0005 inches to 0.00195 inches, 0.001 inches to 0.002 inches, or in some cases approximately 0.0015 inches. Accordingly, a depth of each of the channels 145 defined by adjacent splines 115 may range from about 0.0001 inches to 0.002 inches, more typically about 0.0005 inches to 0.00195 inches, 0.001 inches to 0.002 inches, or in some cases approximately 0.0015 inches. Though recited in terms of certain ranges, it will be understood that all ranges from the lowest of the lower limits to the highest of the upper limits are included, including all intermediate ranges or specific dimensions, within this full range or any specifically recited range.

In some embodiments, the depth of each of the channels tapers in a direction towards the tubing port 120. For example, each of the channels 145 may have a maximum depth in the region adjacent to a second end 155 of the restriction 130. As the channels 145 approach the tubing port 120, the depth of each of the channels 145 may progressively decrease until each channel 145 terminates.

Referring back to FIG. 2, a length of each of the axial splines 115 spans a portion of the length of the inner circumferential surface 112 of the tubing portion 103. In some embodiments, the length of the axial splines 115 spans between about 10% and 90% of the length of the inner circumferential surface 112 of the tubing portion 103, more typically between about 25% and 75%, between about 40% and 60%, or in some cases approximately 50% of the length of the inner circumferential surface 112 of the tubing portion 103. Since the channels 145 are defined between adjacent axial splines 115, the length of each of the channels 145 similarly may spans between about 10% and 90% of the length of the inner circumferential surface 112 of the tubing portion 103, more typically between about 25% and 75%, between about 40% and 60%, or in some cases approximately 50% of the length of the inner circumferential surface 112 of the tubing portion 103. Though recited in terms of certain ranges, it will be understood that all ranges from the lowest of the lower limits to the highest of the upper limits are included, including all intermediate ranges or specific percentages, within this full range or any specifically recited ranges. It is advantageous to ensure that the channels do not extend all the way through the tubing port in order to prevent inadvertent fluid leaks, as well as to prevent solvent from inadvertently leaking out of the tubing portion 103.

Figure 5:
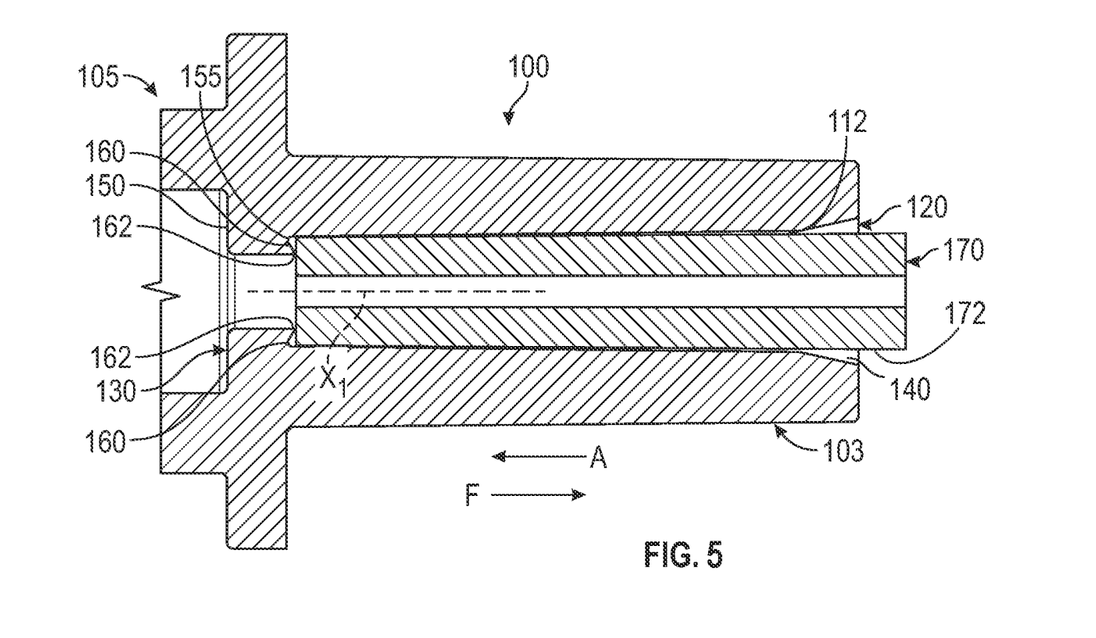
FIG. 5 is a cross-sectional view of the connector of FIG. 2 including a tubing inserted therein, in accordance with some embodiments of the present disclosure.

FIG. 5 is a cross-sectional view of the connector 100 of FIG. 2 including the microbore tubing 170 inserted therein, in accordance with some embodiments of the present disclosure. As previously described, the connector 100 may include a restriction 130. As illustrated in FIG. 5, the restriction 130 may include a first end 150 defined along the luer profile 133 and a second end 155 defined along the tubing profile 135. In the depicted embodiments, the second end 155 may include a radial projection 160 protruding (or otherwise projecting) radially inward and at an angle θ from the inner circumferential surface 112 of the tubing profile 135. The radial projection 160 may be configured to dig into, grip, or otherwise engage a first end of the microbore tubing 170 to create a seal between the second end 155 of the restriction 130 and the microbore tubing 170 to prevent fluid from inadvertently leaking between the external surface 172 of the microbore tubing 170 and the inner circumferential surface 112 defined in the tubing portion 103. In some embodiments, the radial projection 160 is circularly disposed about a central axis $X_1$ of the internal bore 140.

The radial projection 160 may form a sealing ring that prevents fluid from inadvertently leaking between the outer surface of the microbore tubing 170 and the inner circumferential surface 112 defined in the tubing portion 103. In some embodiments, the radial projection 160 may be formed with an undercut so as to sufficiently "bite into" or otherwise engage the first end of the microbore tubing 170.

In some embodiments, a maximum distance by which the radial projection 160 projects into the internal bore 140 is less than or equal to the thickness of the microbore tubing 170. This prevents the radial projection 160 from occluding the fluid travelling the tubing inserted into the connector 100. The restriction 130 may not be restricted to any particular shape or size as long as the restriction 130 prevents the extent of the tubing inserted into the connector 100.

Thus, in some embodiments, the radial projection 160 may also act as a retaining mechanism for improving the ability of the connector 100 to retain the microbore tubing 170 inserted therein and thereby prevent the microbore tubing 170 from separating (or otherwise dislodging) from the connector 100, for example, during a low pressure condition in the tubing created due to a reduction in the fluid in the tubing. In an example, and as illustrated, the radial projection 160 may be disposed at or adjacent the boundary between the tubing portion and the luer portion 105. As depicted, the radial projection 160 may project radially inward a certain distance from the inner circumferential surface 112 into the internal bore 140 defined in the tubing portion 103. In an example, the radial projection 160 may be a spike like structure that extends from the inner circumferential surface 112.

Advantageously, the radial projection 160 may thus be a structure that increases friction between the outer surface of the microbore tubing 170 and the inner circumferential surface 112 such that the microbore tubing 170 may not be easily dislodged from the connector 100, without departing from the scope of the disclosure. In some embodiments, the radial projection 160 may be structured as a ramp that has a slight undercut configured to slightly compress the microbore tubing 170 as it is inserted or advanced into the connector 100. When the microbore tubing 170 is pulled to be withdrawn from the connector, the top of the ramp, and in some embodiments the undercut portion, will secure the microbore tubing 170 within the connector 100 as illustrated in FIG. 5. In some embodiments, the top of the ramp, or the undercut portion, will dig into or grip the microbore tubing 170 when it is attempted to be withdrawn from within the connector 100, as explained further below.

Referring to FIG. 5, with continued reference to FIG. 2, the microbore tubing 170 may be inserted into the connector 100 generally in the direction of arrow A and the radial projection 160 may have a tapered distal end 162 that is generally oriented in the direction in which the microbore tubing 170 is inserted into the connector 100. The microbore tubing 170 may be inserted into the connector 100 with relative ease. However, the radial projection 160 may increase the friction between the connector 100 and the microbore tubing 170 when a tensile force (direction indicated by the arrow F) is applied on the microbore tubing 170 to remove it from the connector 100. Advantageously as a result, the tensile force required to remove or otherwise dislodge the microbore tubing 170 from the connector 100 is increased and thus the microbore tubing 170 is better secured in the connector 100. Further, fluid in the microbore tubing 170 may exert pressure in a radially outward direction, which may further increase the friction between the microbore tubing 170 and the radial projection 160.

It should be noted that the locations of the radial projection on the inner circumferential surface 112 in the Figures are merely examples, and the location may be changed, without departing from the scope of the disclosure. Further, although the Figures indicate one radial projection, the radial projection may be replaced, for example with ledges and/or barbed features, the number of which may not be limited and may be increased or decreased, without departing from the scope of the disclosure. For example, multiple ledges may be disposed at regular intervals along the inner circumferential surface 112 in the tubing portion 103. However, in other embodiments, the ledges may be disposed at irregular intervals along the inner circumferential surface 112. Similarly, multiple barbed features may be disposed at regular intervals along the inner circumferential surface 112 in the tubing portion 103. However, in other embodiments, the barbed features may be disposed at irregular intervals. The circumferential extent of barbed features may be around a quarter of a quadrant of the inner circumferential surface 112. However, in other examples, the circumferential extent of the barbed features may be increased or decreased as required by application or design, and without departing from the scope of the disclosure.

Figure 6:
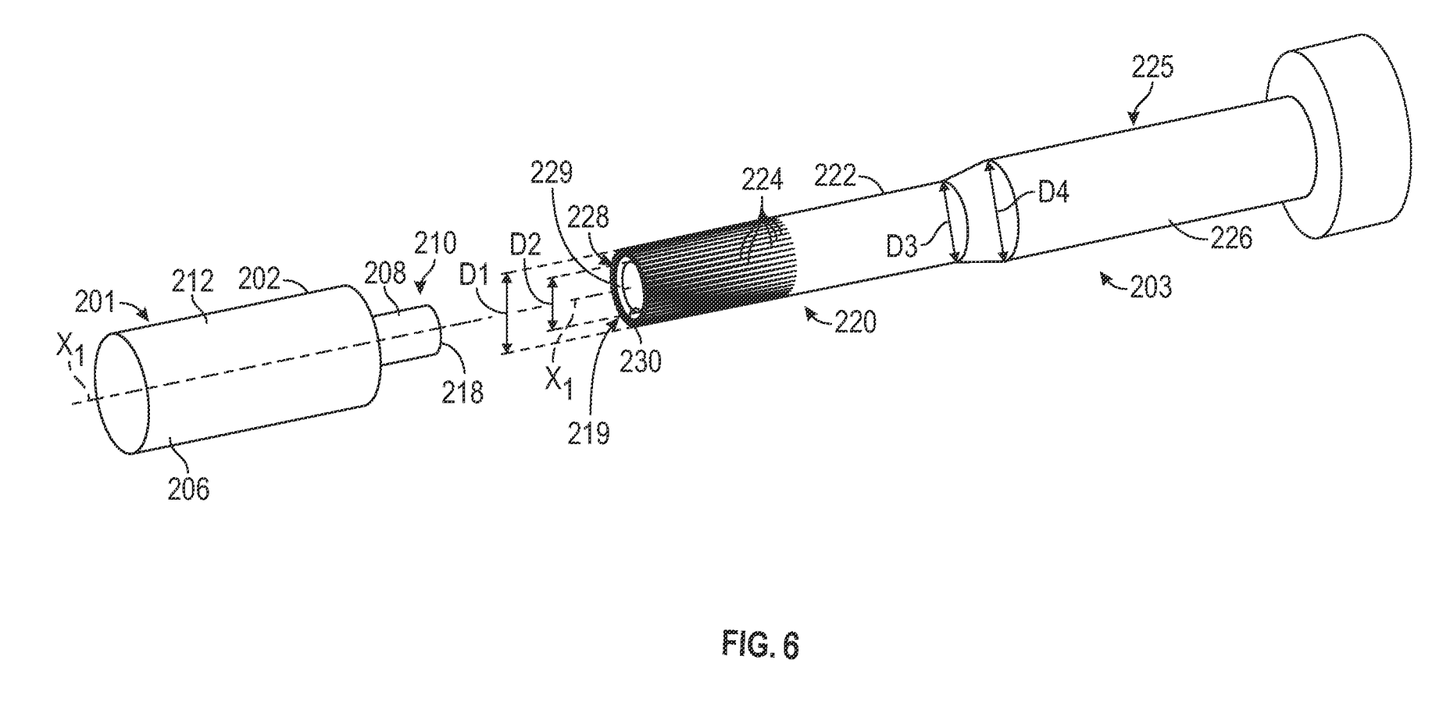
FIG. 6 illustrates core pins used to form the tubing profile and the luer profile on the inner circumferential surface of the connector of FIG. 2, in accordance with some embodiments of the present disclosure.

FIG. 6 illustrates core pins 201 and 203 used to respectively form the tubing profile 135 and the luer profile 133 on the inner circumferential surface 112 of the connector 100 of FIG. 2, in accordance with some embodiments of the present disclosure. In accordance with some embodiments, the connector 100 may be manufactured using an injection molding process. However, other manufacturing processes may also be used to manufacture the connector 100, without departing from the scope of the disclosure. In an example, the core pin 201 may form the luer profile 133 of the inner circumferential surface 112 and the core pin 203 may form the tubing profile 135 of the inner circumferential surface 112. For the sake of brevity, the processing steps and molds used for creating the features (e.g., grip 107) on the outer surface of the body 101 are omitted.

As depicted, core pin 201 has a generally elongated body 202 having a luer-shaping portion 206 and a restriction-shaping portion 208. The luer-shaping portion 206 has a generally cylindrical outer surface 212 having a diameter larger than the diameter of the restriction-shaping portion 208. The outer surface 212 of the luer-shaping portion 206 is shaped to form the luer profile 133 (illustrated in FIG. 2). A restriction-forming profile 210 may be formed on the outer surface 212 proximate a distal end 218 of the luer-shaping portion 206.

In accordance with some embodiments, the core pin 203 also has a generally elongated body having base portion 225 with a cylindrical outer surface 226 and a tubing-shaping portion 220 having a cylindrical outer surface 222. In some embodiments, the diameter D4 of the base portion 225 is greater than the diameter D3 of the tubing-shaping portion 220. The cylindrical outer surface 222 is shaped and sized to form the tubing profile 135 (FIG. 2) of the tubing portion 103. In the depicted embodiments, the cylindrical outer surface 222 of the tubing-shaping portion 220 may be formed with a plurality of axially extending teeth 224 formed along a radial exterior of the outer surface 222. Adjacent teeth 224 may define a recess 215 therebetween. As shall be described below, during manufacturing, the teeth 224 define a shape of the channels 145 and the recesses 215 define a shape of the axial splines 115 of the connector.

In the depicted embodiments, the length of each of the axially extending teeth 224 may span a portion of the length of the inner circumferential surface 112 of the tubing portion 103. In some embodiments, the length of the axially extending teeth 224 spans between about 10% and 90% of the length of the inner circumferential surface 112 of the tubing portion 103, more typically between about 25% and 75%, between about 40% and 60%, or in some cases approximately 50% of the length of the inner circumferential surface 112 of the tubing portion 103. Since the recesses 215 are defined between adjacent axially extending teeth 224, the length of each of the recesses similarly may span between about 10% and 90% of the length of the inner circumferential surface 112 of the tubing portion 103, more typically between about 25% and 75%, between about 40% and 60%, or in some cases approximately 50% of the length of the inner circumferential surface 112 of the tubing portion 103. Though recited in terms of certain ranges, it will be understood that all ranges from the lowest of the lower limits to the highest of the upper limits are included, including all intermediate ranges or specific percentages, within this full range or any specifically recited ranges.

Figure 7:
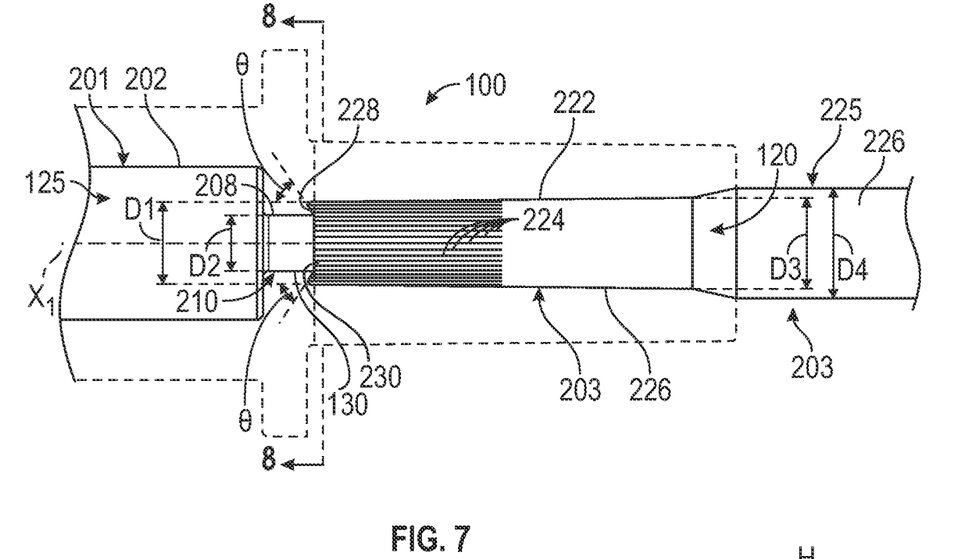
FIG. 7 is a cutaway view of the connector (illustrated in phantom) of FIG. 2 including the core pins of FIG. 6 disposed therein, in accordance with some embodiments of the present disclosure.
Figure 8:
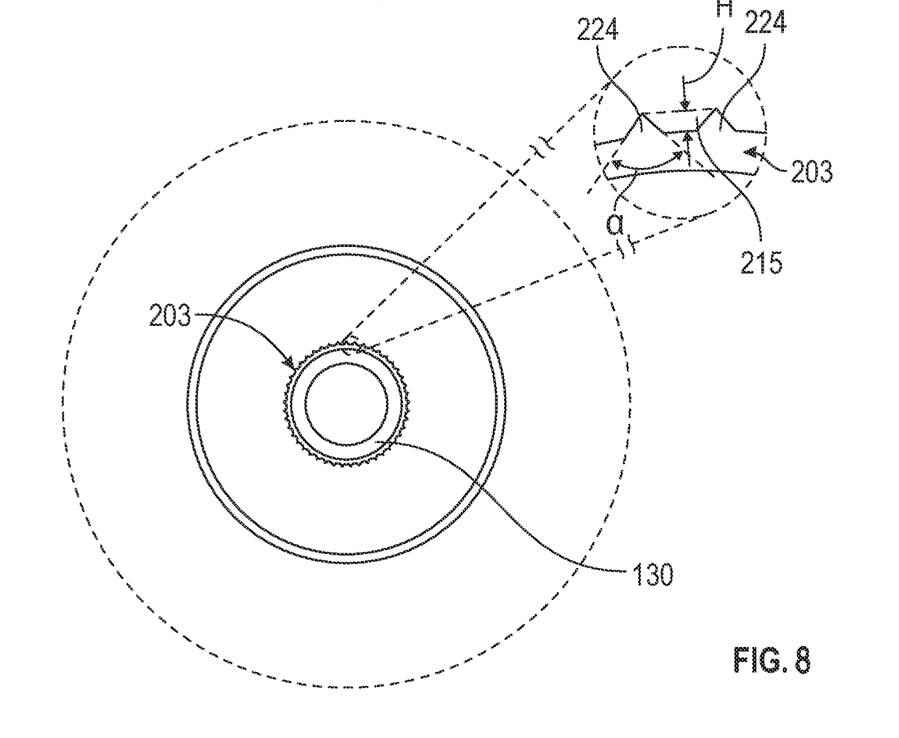
FIG. 8 is a cross-sectional view along line 8-8 of FIG. 7, in accordance with some embodiments of the present disclosure.

FIG. 7 is a cutaway view of the connector (illustrated in phantom) of FIG. 2 including the core pins 201 and 203 of FIG. 6 disposed therein, in accordance with some embodiments of the present disclosure. FIG. 8 is a cross-sectional view of the connector 100 and core pin 203 taken along line 8-8 of FIG. 7, in accordance with some embodiments of the present disclosure. In accordance with some embodiments, the connector 100 may be manufactured using an injection molding process. The connector 100 may be made of plastic or similar material that can be molded into a desired shape. An external mold (not illustrated) may be used to create the external features of the connector 100. These external features may include the grip 107, and the outer surface of the cylindrical body 101. The internal bore 140, tubing profile 135, the luer profile 133, the restriction 130, and the radial projection 160 may be formed using the core pins 201 and 203.

During manufacture, material forming the connector 100 may be placed in a molding tool including the core pins 201 and 203 axially aligned with each other. The core pins 201 and 203 may be brought together from axially opposite ends into the material. The material may be in a semi-solid, malleable state in order to mold it into a desired shape. The core pins 201 and 203 may be brought towards each other until the core pins 201 and 203 couple to each other, as illustrated in FIG. 7.

Referring back to FIG. 6, the distal end 219 of the tubing-shaping portion 220 of the core pin 203 may include radial projection-forming profile 228 including formed as a ring having an inner surface 229 angled radially inward and a cavity 230 defined therethrough. When the core pins 201 and 203 are coupled to each other, the distal end 218 of the core pin 201 is received partially into the cavity 230 defined by the radial projection-forming profile 228. In particular, as depicted, the distal end 218 of the core pin 201 is disposed concentrically with, and radially interior to the inner surface 229 of the radial projection-forming profile 228. The restriction-shaping portion 208 and the radial projection-forming profile 228 cooperatively form the restriction 130 and the radial projection. Specifically, when the core pins 201 and 203 are coupled to each other, a void is formed between the restriction-shaping portion 208 and the radial projection-forming profile 228. The void is filled with the semi-solid, malleable connector material and molded into the shape of the void (i.e. the shape of the radial projection 160).

Furthermore, during manufacture, when the core pins 201 and 203 are coupled to each other and the semi-solid, malleable connector material is placed in the molding tool including the core pins 201 and 203 axially aligned with each other, the axially extending teeth 224 may pierce into the semi-solid, malleable connector material and form an imprint therein. The semi-solid, malleable connector material may also fill the recesses 215 and be molded into a shape defined by the recesses 215. Once the semi-solid, malleable connector material has solidified, the core pins 201 and 203 are removed. When the core pin 203 is removed axially extending recesses are created along the inner circumferential surface 112 of the tubing portion 103 where the axially extending teeth 224 pierced into the connector material. The axially extending channels correspond to the axially extending channels 145 in the tubing profile 135 of the tubing portion 103. Similarly, when the core pin 203 is removed axially extending splines project along the inner circumferential surface 112 of the tubing portion 103 where the semi-solid, malleable connector material filled the recesses 215. The filled recesses 215 correspond to the axial splines 115 formed on the tubing profile 135 of the tubing portion 103.

As previously described, in some embodiments, the depth of each of the channels 145 tapers in a direction towards the tubing port 120. The tapering of the depth of each of the channels 145 is due to the configuration of the tubing profile 135. For example, as depicted, the diameter D1 of the internal bore 140 at the end of the tubing profile 135 adjacent to the restriction 130 is smaller than the diameter D2 of internal bore 140 at the end of the tubing profile 135 adjacent to the tubing port 120. As such, the tubing profile 135 tapers in a direction from the end adjacent to the tubing port 120 to the end adjacent to the restriction 130. When the core pin 203 having the axially extending teeth 224 is positioned in the mold with the material used to form the connector 100, the teeth 224 dig deeper into the connector material in the area of the tubing profile adjacent to the restriction 130 (due to the smaller diameter D1) and dig progressively less into the connector material in the direction of the tubing port 120 (due to the diameter increasing to D2 in the direction of the tubing port). Since the teeth 224 dig deeper into the connector material in the area of the tubing profile 135 adjacent to the restriction 130, the resulting channels 145 have a greater depth and the resulting axial splines have a greater height in this area than in the area approaching the tubing port 120.

The aforementioned configuration is advantageous in that axial splines 115 are able to bite into or grip the microbore tubing 170 to a greater degree in the area of the tubing profile adjacent to the restriction 130, thereby necessitating a relatively stronger tensile force to be exerted on the microbore tubing 170 to separate or dislodge the microbore tubing 170 from the connector 100. Thus, accidental separation of the microbore tubing 170 from the connector 100 may be minimized.

In accordance with some embodiments, the axial splines 115 and channels 145 may be disposed at regular intervals along the inner circumferential surface 112 of the tubing portion 103. However, in other embodiments, the axial splines 115 and channels 145 may be disposed at irregular intervals along the inner circumferential surface 112 of the tubing profile 135.

In accordance with some embodiments, an angle $\alpha$ between the first inclined side 117 and the second inclined side 119 of adjacent splines ranges from about 30 degrees to 150 degrees, more typically about 60 degrees to 120 degrees, and 80 degrees to 100 degrees, or in some cases approximately 90 degrees. Though recited in terms of certain ranges, it will be understood that all ranges from the lowest of the lower limits to the highest of the upper limits are included, including all intermediate ranges or specific angles, within this full range or any specifically recited range.

In some embodiments, similar to the axial splines 115, a depth of each of the recesses 215 may range from about 0.0001 inches to 0.002 inches, more typically about 0.0005 inches to 0.00195 inches, 0.001 inches to 0.002 inches, or in some cases approximately 0.0015 inches. Accordingly, similar to the axial channels 145, a height H of each of the axially extending teeth 224 may range from about 0.0001 inches to 0.002 inches, more typically about 0.0005 inches to 0.00195 inches, 0.001 inches to 0.002 inches, or in some cases approximately 0.0015 inches. Though recited in terms of certain ranges, it will be understood that all ranges from the lowest of the lower limits to the highest of the upper limits are included, including all intermediate ranges or specific dimensions, within this full range or any specifically recited range.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A connector comprising:
   a body having a tubing port and a luer port;
   an internal bore extending axially between the tubing port and the luer port;
   a plurality of axial splines extending linearly along a first portion of the internal bore; and
   a plurality of axial channels disposed between the plurality of axial splines,
   wherein a depth of each axial channel of the plurality of axial channels tapers in a direction towards the tubing port, and
   wherein edges of the plurality of axial splines are configured to engage and grip an external surface of a tubing to retain the tubing in the body.

2. The connector of claim 1, wherein each axial channel of the plurality of axial channels comprises a recess extending axially along the first portion of the internal bore.

3. The connector of claim 2, wherein each recess has a depth ranging from about 0.0001 inches to 0.002 inches.

4. The connector of claim 1, wherein a height of each axial spline of the plurality of axial splines ranges from about 0.0001 inches to 0.002 inches.

5. The connector of claim 1, wherein an angle between sides of adjacent axial splines of the plurality of axial splines ranges from about 30 degrees to 150 degrees.

6. The connector of claim 1, wherein the tubing comprises microbore tubing.

7. The connector of claim 1, wherein the plurality of axial splines are equally spaced apart from each other about the first portion of the internal bore.

8. The connector of claim 1, further comprising a tubing portion, wherein the tubing portion comprises the first portion of the internal bore and a second portion of the internal bore disposed between the first portion of the internal bore and the tubing port.

9. The connector of claim 8, wherein a length of each axial spline of the plurality of axial splines spans half or less of a length of the tubing portion.

10. The connector of claim 1, wherein a height of each axial spline of the plurality of axial splines tapers in the direction towards the tubing port.

11. The connector of claim 1, wherein the plurality of axial channels are configured to contain a solvent therein, and wherein the solvent is configured to bond the external surface of the tubing to the first portion of the internal bore.

12. The connector of claim 1, the body further comprising a restriction portion of the internal bore disposed at an end of the first portion of the internal bore furthest from the tubing port, the restriction portion extending radially inward beyond an inner surface of the first portion of the internal bore.

13. The connector of claim 12, wherein the restriction portion comprises a radial projection extending at an acute angle from the inner surface of the first portion, the radial projection configured to create a seal between the restriction portion and the tubing.

14. The connector of claim 13, wherein the radial projection is circularly disposed about a central axis of the internal bore and configured to bite into the tubing to create the seal between the restriction portion and the tubing.

* * * * *